United States Patent
Kugler et al.

(10) Patent No.: US 9,943,314 B2
(45) Date of Patent: Apr. 17, 2018

(54) MAGNETICALLY-DRIVEN DELIVERY ASSEMBLY AND METHOD

(71) Applicant: Teleflex Innovations S.à.r.l., Luxembourg (LU)

(72) Inventors: Chad Kugler, Buffalo, MN (US); James Murto, Maple Grove, MN (US)

(73) Assignee: Teleflex Innovations S.à.r.l., Luxembourg (LU)

( * ) Notice: Subject to any disclaimer, the term of this patent is extended or adjusted under 35 U.S.C. 154(b) by 251 days.

(21) Appl. No.: 15/004,012

(22) Filed: Jan. 22, 2016

(65) Prior Publication Data
US 2016/0302796 A1  Oct. 20, 2016

Related U.S. Application Data

(60) Provisional application No. 62/147,008, filed on Apr. 14, 2015.

(51) Int. Cl.
| | | |
|---|---|---|
| *A61M 29/00* | (2006.01) | |
| *A61B 17/12* | (2006.01) | |
| *A61B 17/00* | (2006.01) | |

(52) U.S. Cl.
CPC .... *A61B 17/12109* (2013.01); *A61B 17/1219* (2013.01); *A61B 2017/00477* (2013.01);
(Continued)

(58) Field of Classification Search
CPC .......... A61B 17/12109; A61B 17/1219; A61B 2017/12086; A61B 2017/00876; A61B 2017/00477
(Continued)

(56) References Cited

U.S. PATENT DOCUMENTS

| | | |
|---|---|---|
| 4,755,184 A | 7/1988 | Silverberg |
| 4,766,405 A | 8/1988 | Daly et al. |

(Continued)

FOREIGN PATENT DOCUMENTS

| | | |
|---|---|---|
| EP | 1490138 B1 | 12/2008 |
| EP | 1572287 B1 | 2/2011 |

(Continued)

OTHER PUBLICATIONS

Office Action dated Jun. 9, 2016, in Canadian Patent Application No. 2817242.
(Continued)

*Primary Examiner* — Amy R Weisberg
(74) *Attorney, Agent, or Firm* — Gregory W. Smock

(57) ABSTRACT

Assemblies and methods for delivering an implant to a patient are disclosed. A delivery assembly can comprise an elongate tube, an outer magnetic member, and an inner magnetic member. The elongate tube extends from a proximal end portion to a distal end portion and defines a delivery lumen. The outer magnetic member can be movable along an outer surface of the tube; the inner magnetic member can be positioned within the delivery lumen and magnetically coupled to the outer magnetic member through a sidewall of the tube. The inner magnetic member can be movable through the delivery lumen when actuated by relative movement between the outer magnetic member and the tube. The delivery assembly can further comprise a syringe or an inflator/deflator couplable to a hub at the proximal end portion of the tube. The syringe or inflator/deflator can be used to urge fluid against a proximal end portion of the inner magnetic member.

22 Claims, 11 Drawing Sheets

(52) U.S. Cl.
CPC ............... *A61B 2017/00876* (2013.01); *A61B 2017/12086* (2013.01)

(58) Field of Classification Search
USPC .............................. 623/1.11–1.23; 600/9, 12
See application file for complete search history.

(56) References Cited

U.S. PATENT DOCUMENTS

| | | | |
|---|---|---|---|
| 4,959,056 A | 9/1990 | Dombrowski et al. | |
| 5,320,639 A | 6/1994 | Rudnick | |
| 5,456,693 A | 10/1995 | Conston et al. | |
| 5,522,840 A | 6/1996 | Krajicek | |
| 5,584,803 A | 12/1996 | Stevens et al. | |
| 5,674,204 A | 10/1997 | Chanoch | |
| 5,728,062 A | 3/1998 | Brisken | |
| 7,255,684 B2* | 8/2007 | Zubry | A61M 5/24 604/131 |
| 7,303,571 B2 | 12/2007 | Makower et al. | |
| 7,465,318 B2 | 12/2008 | Sennett et al. | |
| 7,582,110 B2 | 9/2009 | Case et al. | |
| 7,618,435 B2 | 11/2009 | Opolski | |
| 7,712,470 B2 | 5/2010 | Gertner | |
| 7,815,661 B2 | 10/2010 | Mirizzi et al. | |
| 7,842,054 B2 | 11/2010 | Greene et al. | |
| 7,955,343 B2 | 6/2011 | Makower et al. | |
| 8,029,560 B2 | 10/2011 | Bates et al. | |
| 8,100,934 B2 | 1/2012 | Darnis et al. | |
| 8,128,682 B2 | 3/2012 | Case et al. | |
| 8,333,786 B2 | 12/2012 | Mirizzi et al. | |
| 8,758,427 B2 | 6/2014 | Root et al. | |
| 9,351,736 B2 | 5/2016 | Root et al. | |
| 2002/0022807 A1 | 2/2002 | Duchon et al. | |
| 2003/0153972 A1 | 8/2003 | Helmus | |
| 2004/0176797 A1* | 9/2004 | Opolski | A61B 17/12022 606/213 |
| 2004/0256584 A1 | 12/2004 | Zimmerling et al. | |
| 2006/0212127 A1 | 9/2006 | Karabey et al. | |
| 2006/0229668 A1 | 10/2006 | Prestezog et al. | |
| 2006/0276882 A1 | 12/2006 | Case et al. | |
| 2007/0005021 A1 | 1/2007 | Kohlbrenner et al. | |
| 2007/0166345 A1 | 7/2007 | Pavcnik et al. | |
| 2007/0292472 A1 | 12/2007 | Paul et al. | |
| 2007/0293932 A1 | 12/2007 | Zilla et al. | |
| 2008/0243068 A1 | 10/2008 | Ramzipoor et al. | |
| 2009/0062772 A1 | 3/2009 | Wakeford et al. | |
| 2009/0069758 A1 | 3/2009 | Bates et al. | |
| 2009/0093822 A1* | 4/2009 | Ducharme | A61F 2/95 606/108 |
| 2010/0036399 A1 | 2/2010 | Viola | |
| 2010/0106178 A1 | 4/2010 | Obermiller et al. | |
| 2010/0274280 A1 | 10/2010 | Sawhney et al. | |
| 2011/0005062 A1 | 1/2011 | Greene et al. | |
| 2011/0066183 A1 | 3/2011 | Sawhney et al. | |
| 2011/0077683 A1 | 3/2011 | Huss | |
| 2011/0152902 A1 | 6/2011 | Kurrus et al. | |
| 2012/0245614 A1 | 9/2012 | Drasler | |
| 2012/0259155 A1 | 10/2012 | Ishikawa et al. | |
| 2013/0144323 A1 | 6/2013 | Root et al. | |
| 2014/0350590 A1 | 11/2014 | Root et al. | |
| 2015/0238196 A1 | 8/2015 | Root et al. | |
| 2016/0158041 A1* | 6/2016 | Roeder | A61F 2/86 623/1.11 |
| 2017/0128072 A1* | 5/2017 | Wang | A61B 17/11 |

FOREIGN PATENT DOCUMENTS

| | | |
|---|---|---|
| EP | 2192885 B1 | 2/2013 |
| EP | 2673014 A1 | 12/2013 |
| EP | 2673014 B1 | 5/2016 |
| WO | 2005016434 A1 | 2/2005 |
| WO | 2009029869 A2 | 3/2009 |
| WO | 2010096717 A1 | 8/2010 |
| WO | 2011077750 A1 | 6/2011 |
| WO | 2013026850 A1 | 2/2013 |
| WO | 2013081768 A1 | 6/2013 |
| WO | 2014001310 A1 | 1/2014 |

OTHER PUBLICATIONS

"International application serial No. PCT/US2012/063101, International Preliminary Report on Patentability dated Jun. 12, 2014", 8 pgs.

"International application serial No. PCT/US2012/063101, International Search Report dated Feb. 25, 2013", 6 pgs.

"International application serial No. PCT/US2012/063101, Written Opinion dated Feb. 25, 2013", 6 pgs.

* cited by examiner

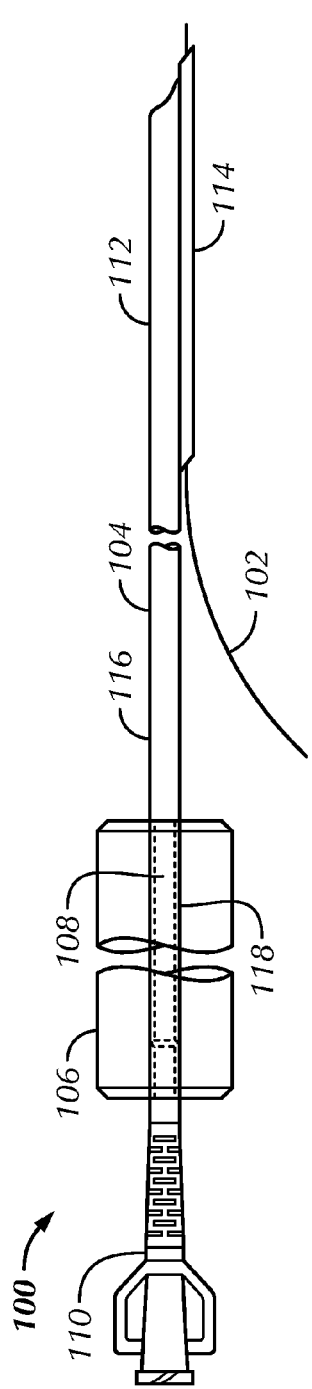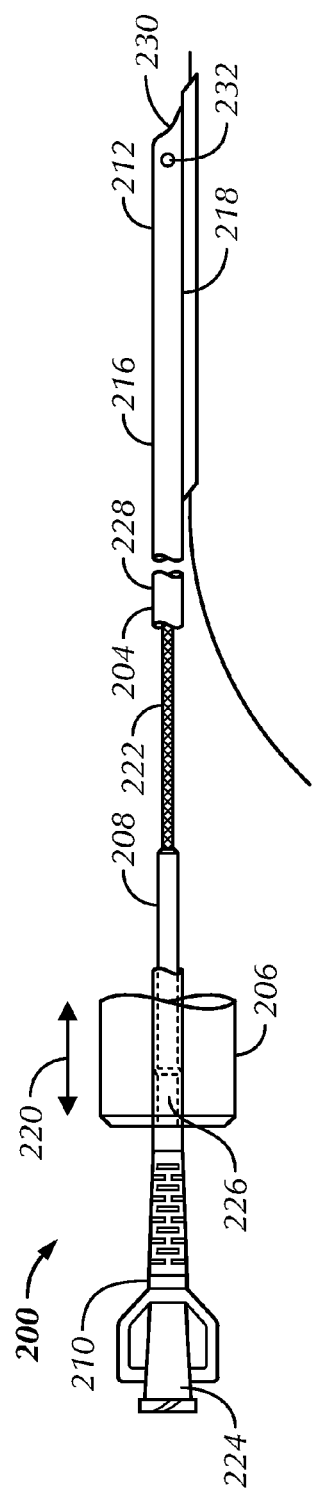

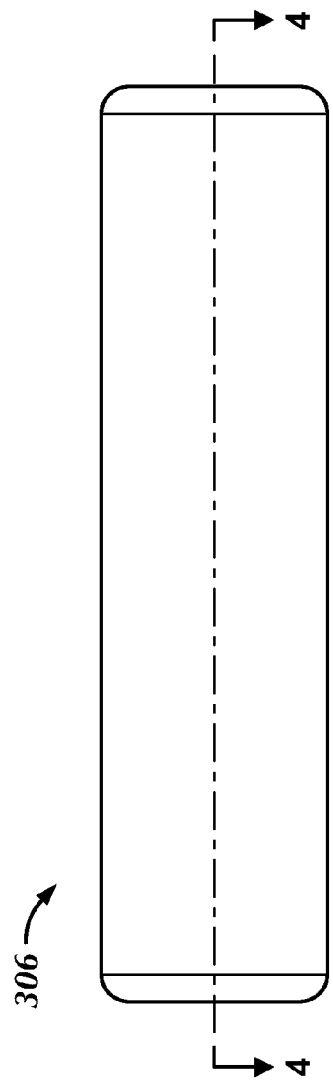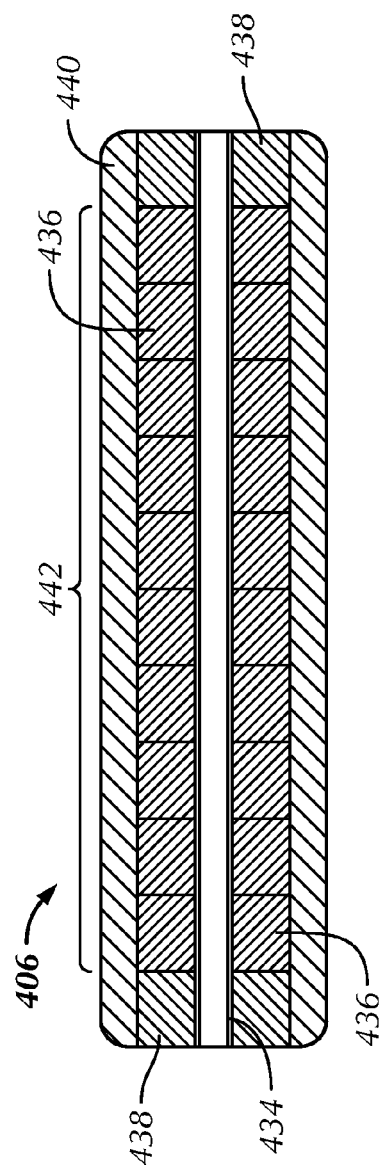

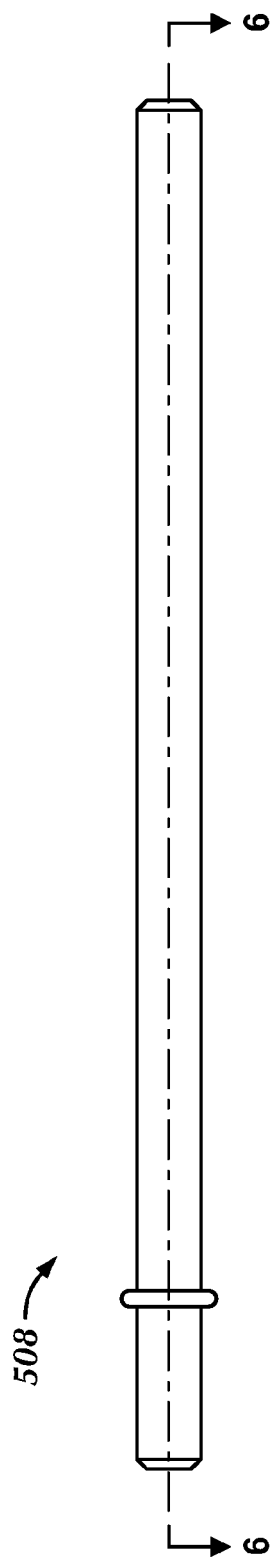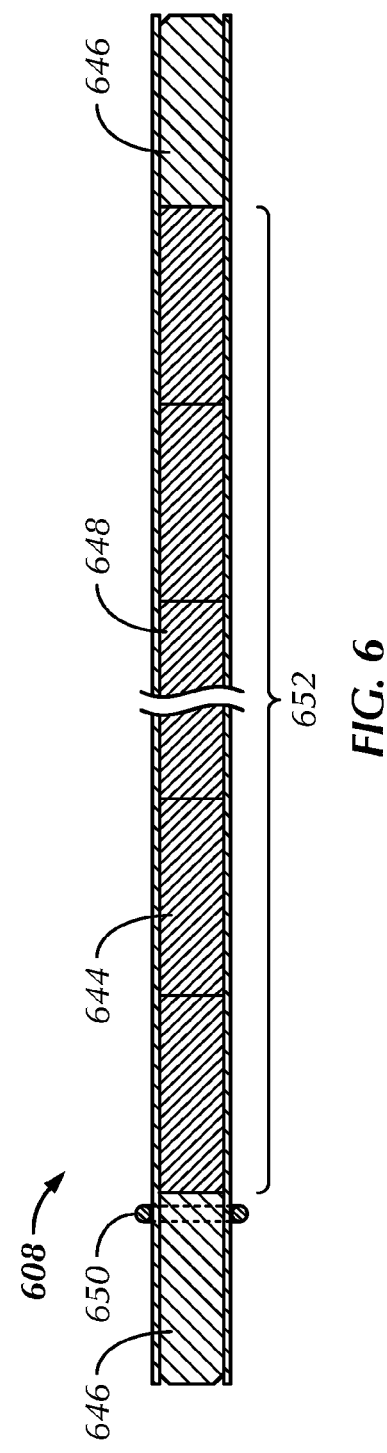
FIG. 5
FIG. 6

MAGNETICALLY-DRIVEN DELIVERY ASSEMBLY AND METHOD

CLAIM OF PRIORITY

This non-provisional patent document claims the benefit of priority under 35 U.S.C. § 119(e) to U.S. Provisional Patent Application Ser. No. 62/147,008, entitled "MAGNETICALLY-DRIVEN DELIVERY ASSEMBLY AND METHOD" and filed on Apr. 14, 2015, which is herein incorporated by reference in its entirety.

TECHNICAL FIELD

This patent document relates to medical devices. More particularly, but not by way of limitation, the patent document relates to assemblies, kits and methods for delivering an implant to a subject.

BACKGROUND

Medical implants can be delivered into a defect site or target region within a patient using a delivery device. One type of delivery device used to deliver a medical implant includes a barrel and a plunger. The implant can be advanced into the defect site or target region by depressing the plunger.

OVERVIEW

The present inventors recognize that a problem faced by physicians when handling elongate or expandable implants relates to delivery into a patient. In order to discharge an implant using a delivery device including a barrel and a plunger, a physician must apply force to the plunger to cause distal movement of the implant. The force that must be applied to distally move elongate or expandable implants can exceed the capabilities of the physician. This can particularly be the case when an elongate implant is configured to expand when exposed to bodily fluids, in which case the force applied to the plunger has to overcome longitudinal friction associated with the implant's length and radial friction associated with the implant's expansion. The present assemblies, kits and methods include a magnetic arrangement providing assistance to the physician when delivering elongate or expandable implants into the patient.

A present assembly for delivering elongate or expandable implants can comprise an elongate tube, an outer magnetic member, and an inner magnetic member. The elongate tube extends from a proximal end portion to a distal end portion and defines a delivery lumen. The outer magnetic member can be movable along an outer surface of the tube; the inner magnetic member can be positioned within the delivery lumen and magnetically coupled to the outer magnetic member through a sidewall of the tube. The inner magnetic member can be movable through the delivery lumen when actuated by relative movement between the outer magnetic member and the tube. The delivery assembly can further comprise a syringe or an inflator/deflator couplable to a hub at the proximal end portion of the tube. The syringe or inflator/deflator can be used to urge fluid against a proximal end portion of the inner magnetic member.

A present kit can include an elongate tube preloaded with an inner magnetic member and an implant, an outer magnetic member, and instructions for delivering the implant into a patient. Optionally, the kit further includes a guidewire that, when placed within the patient, guides a distal end portion of the elongate tube and the implant to a defect site or target region within a vascular vessel.

A present method for delivering elongate or expandable implants can comprise accessing a vascular vessel by piercing an opening and inserting a guidewire into the opening. The guidewire can be advanced through a portion of the vascular vessel to a defect site or target region. A distal end portion of an elongate tube and an implant, which is positioned within a delivery lumen of the tube, can be inserted into the vascular vessel and advanced to the defect site or target region. Once at the defect site or target region, relative movement between the inner magnetic member, which is positioned within the delivery lumen and proximal to the implant, and the tube can be generated to urge portions of the implant out the distal end portion of the tube and into the vascular vessel.

These and other examples and features of the present assemblies, kits and methods will be set forth, at least in part, in the following Detailed Description. This Overview is intended to provide non-limiting examples of the present subject matter—it is not intended to provide an exclusive or exhaustive explanation. The Detailed Description below is included to provide further information about the present assemblies, kits and methods.

BRIEF DESCRIPTION OF THE DRAWINGS

In the drawings, like numerals can be used to describe similar features and components throughout the several views. The drawings illustrate generally, by way of example but not by way of limitation, various embodiments discussed in this patent document.

FIG. 1 schematically illustrates portions of a delivery assembly advanceable over a guidewire, as constructed in accordance with at least one embodiment.

FIG. 2 schematically illustrates partial, staggered cutaways of a delivery assembly, as constructed in accordance with at least one embodiment.

FIG. 3 illustrates an outer magnetic member of a delivery assembly, as constructed in accordance with at least one embodiment.

FIG. 4 illustrates, in cross-section, an outer magnetic member of a delivery assembly, as constructed in accordance with at least one embodiment.

FIG. 5 illustrates an inner magnetic member of a delivery assembly, as constructed in accordance with at least one embodiment.

FIG. 6 illustrates, in cross-section, an inner magnetic member of a delivery assembly, as constructed in accordance with at least one embodiment.

Figure 7A:
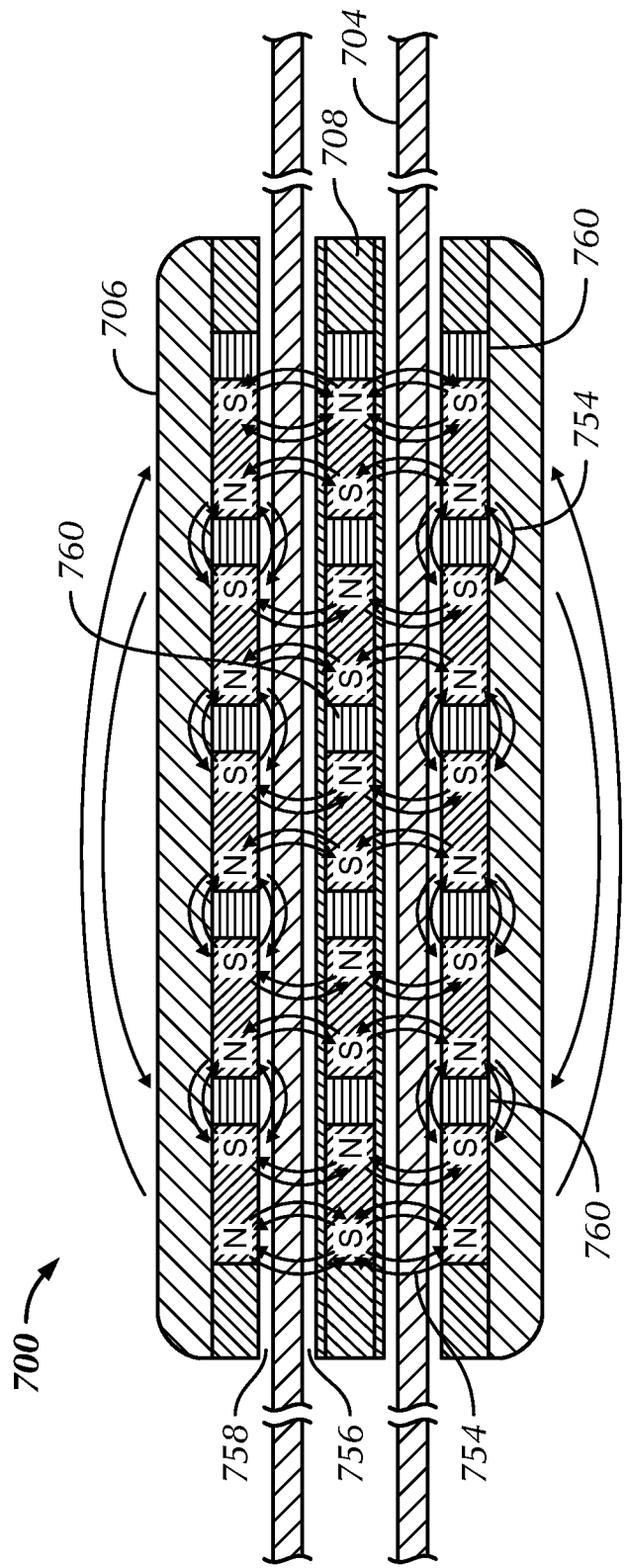
FIGS. 7A-7D schematically illustrate, in cross-section, portions of a delivery assembly and associated magnetic field lines, as constructed in accordance with at least four embodiments.

The drawing figures are not necessarily to scale. Certain features and components may be shown exaggerated in scale or in schematic form, and some details may not be shown in the interest of clarity and conciseness.

DETAILED DESCRIPTION

FIG. 1 illustrates portions of a delivery assembly 100 advanceable over a guidewire 102. The assembly 100 can include an elongate tube 104, an outer magnetic member 106, and an inner magnetic member 108. The tube 104 extends from a proximal end portion 110 to a distal end portion 112 and can have a length in a range of about 10 centimeters (cm) to about 150 cm, for example. The distal end portion 112 of the tube 104 can include a rapid exchange lumen 114 that is sized and shaped to be advanced over the guidewire 102 and guided to a defect site or target region within a vascular vessel. A delivery lumen 116 can be disposed within the tube 104 and longitudinally extends from the proximal end portion 110 to the distal end portion 112. The tube 104 can have a circular cross-section.

The outer magnetic member 106 can be positioned at least partially around the tube 104, and the inner magnetic member 108 can be positioned within the delivery lumen 116. The outer magnetic member 106 and the inner magnetic member 108 can have a circular cross-sectional shape similar to the tube 104. The inner surface of the outer magnetic member 106 can be closely fitted around the outer surface of the tube 104 and be slidable along the tube. The outer surface of the inner magnetic member 108 can be closely fitted to the inner surface of the tube 104 and be slidable within the delivery lumen 116.

The inner magnetic member 108 can be polarized with respect to the outer magnetic member 106 such that the members attract one another through a sidewall 118 of the tube 104. The inner magnetic member 108 can be movable through the delivery lumen 116 when actuated by relative movement between the outer magnetic member 106 and the tube 104. For example, a movement of the outer magnetic member 106 along the outer surface of the tube 104 can cause a corresponding movement of the inner magnetic member 108 within the delivery lumen 116.

FIG. 2 illustrates partial, staggered cutaways of a delivery assembly 200. An outer magnetic member 206 can be arranged over an elongate tube 204 and movable in an axial direction 220. The outer magnetic member 206 can include at least one magnet in the form of a ring magnet (FIG. 4). An inner magnetic member 208, for interacting with the outer magnetic member 206, can be arranged within a delivery lumen 216 of the tube 204. The inner magnetic member 208 can include at least one magnet in the form of a cylindrical magnet (FIG. 6).

Figure 11:
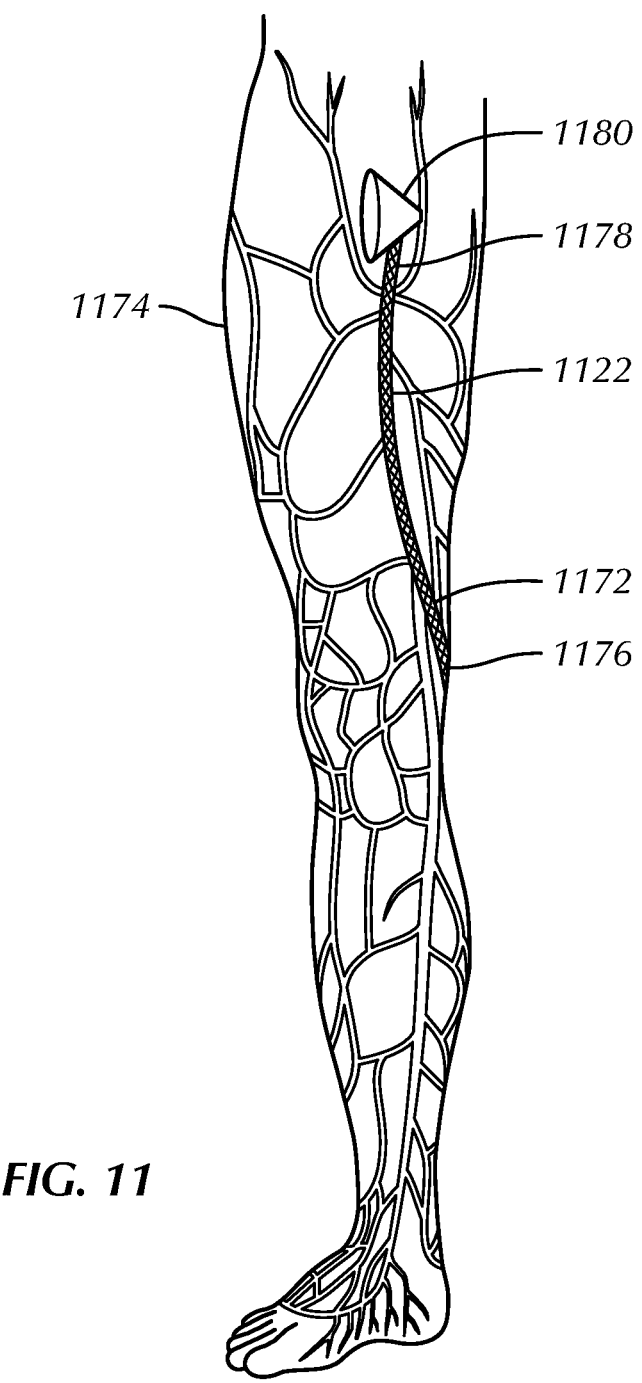
FIG. 11 schematically illustrates implantation of an elongate and expandable implant in portions of a great saphenous vein.

The delivery assembly 200 can further include an elongate or expandable implant 222 positioned within the delivery lumen 216, distal to the inner magnetic member 208. The implant 222 material can be in gas, powder, liquid or solid form and can be of an expandable or non-expandable nature. In an example, the implant 222 includes an elongate and expandable member for occluding a vascular vessel (FIG. 11). The length of the tube 204 can determine how deep into the vascular vessel the implant 222 is placed.

The inner magnetic member 208 can act on the implant 222 and can be driven to discharge the implant 222 from a distal end portion 212 of the tube 204 by the outer magnetic member 206 and/or a compression actuator (e.g., a syringe or inflator/deflator) couplable to a hub 224 at the tube's proximal end portion 210. The distal end portion 212 of the tube 204 can include a skived opening 230 providing a larger discharge opening for the implant 222. In an example, the implant 222 can be discharged from the tube 204 and delivered to a defect site or target region by moving the outer magnetic member 206 distally along the outer surface of the tube 204. The movement of the outer magnetic member 206 can cause corresponding distal movement of the inner magnetic member 208 through the delivery lumen 216. In another example, the implant 222 can be discharged from the tube 204 by applying a force to a proximal end portion 226 of the inner magnetic member 208 using the compression actuator while maintaining a stationary position of the outer magnetic member 206. The stationary positioning of the outer magnetic member 206 can maintain a position of the inner magnetic member 208 via magnetic coupling, while the force applied by the compression actuator against the proximal end portion 226 of the inner magnetic member 208 can cause intermediate 228 and distal end 212 portions of the tube 204 to move proximally, thereby unsheathing the implant 222.

The compression actuator can include a pump or other means of applying a fluid force to the proximal end portion 226 of the inner magnetic member 206. In varying examples, the fluid force applied is sufficient to effect proximal movement of portions of the tube 204 and can be maintained until the inner magnetic member 208 and the implant 222 near the distal end portion 212 of the tube 204. At the distal end portion 212, the hydraulic pressure caused by the applied fluid force can be dissipated by one or more holes 232 in a sidewall 218 of the tube. The dissipation holes 232 can ensure that the inner magnetic member 208 is not discharged from the tube 204 along with the implant 222 as a result of hydraulic pressure on the proximal end portion 226 of the inner magnetic member 208.

FIG. 3 illustrates an elevational view of an outer magnetic member 306. The outer magnetic member 306 can have any suitable size and shape that allows movement about a portion of an elongate tube and handling by a physician. In an example, the outer magnetic member 306 is in the shape of a cylinder.

FIG. 4 illustrates a cross-sectional view of an outer magnetic member 406, such as along line 4-4 of FIG. 3. The outer magnetic member 406 can include, from inside-out, an inner hypotube 434, a plurality of ring magnets 436 and two end plugs 438, and an outer tube 440.

The inner diameter of the hypotube 434 can be selected based on the outer diameter of an elongate tube. The inner diameter of the hypotube 434 is greater than the outer diameter of the tube so that the outer magnetic member 406 can slide along the tube.

Figure 7B:
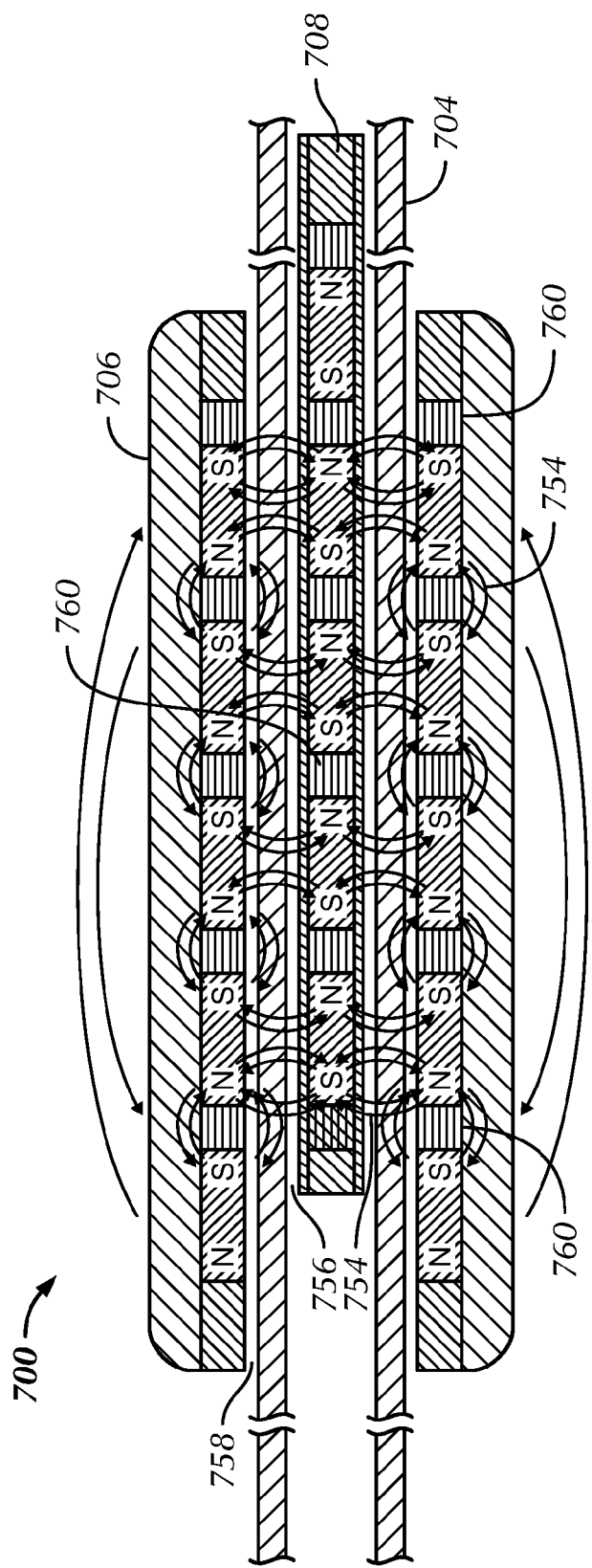

The plurality of ring magnets 436 can include, for example, ten permanent magnets positioned on the hypotube 434, with the hypotube extending through a hole in the center of each magnet. The permanent magnets can comprise one or more of neodymium, samarium cobalt, ceramic, or alnico and can form a magnetic field without the influence of an externally induced magnetic field. Neodymium, for example, is a small and lightweight magnetic material that provides high magnetic flux for its size and weight. The ring magnets 436 can be grouped together to form a magnetic stack 442, which provides greater attractive strength than a single magnet. The magnetic stack 442 can be bounded on each end by the end plugs 438. Optionally, as shown in FIGS. 7A and 7B, one or more ring magnets 436 can be separated from adjacent magnets with a non-magnetic spacer.

The inner diameter of the outer tube 440 can be selected based on the outer diameter of the ring magnets 436, while the outer diameter of the tube 440 can be based on the average size of a human adult hand. The outer diameter of the tube 440 can be sized for grasping or other handling by a physician.

FIG. 5 illustrates an elevational view of a magnetically responsive inner magnetic member 508. The inner magnetic member 508 can have any suitable size and shape that allows movement within a delivery lumen of an elongate tube, while providing a sufficient seal between the inner magnetic member and the inner surface of the elongate tube. The seal should allow for discharge of an implant without allowing implant material or compression actuator fluid to pass to the respective other side of the inner magnetic member 508. In an example, the inner magnetic member 508 is in the shape of a cylinder.

FIG. 6 illustrates a cross-sectional view of an inner magnetic member 608, such as along line 6-6 of FIG. 5. The inner magnetic member 608 can include a plurality of cylindrical magnets 644, two end plugs 646, and an outer hypotube tube 648. Optionally, the inner magnetic member 608 can further include an elastomeric member (e.g., an O-ring) 650 providing the seal between the inner magnetic member 608 and the inner surface of the elongate tube. The elastomeric member 650 can be situated within an annular groove of the inner magnetic member 608.

The plurality of cylindrical magnets 644 can include, for example, ten permanent magnets. The permanent magnets can comprise one or more of neodymium, samarium cobalt, ceramic, or alnico and form a magnetic field without the influence of an externally induced magnetic field. The cylindrical magnets 644 can be grouped together to form a magnetic stack 652. The magnetic stack 652 can be bounded on each end by the end plugs 646. Optionally, as shown in FIGS. 7A and 7B, one or more cylindrical magnets 644 can be separated from adjacent magnets with a non-magnetic spacer.

The outer diameter of the hypotube 648 can be selected based on the inner diameter of the elongate tube. The outer diameter of the hypotube 648 is less than the inner diameter of the tube so that the inner magnetic member 608 can slide within the delivery lumen.

Figure 7C:
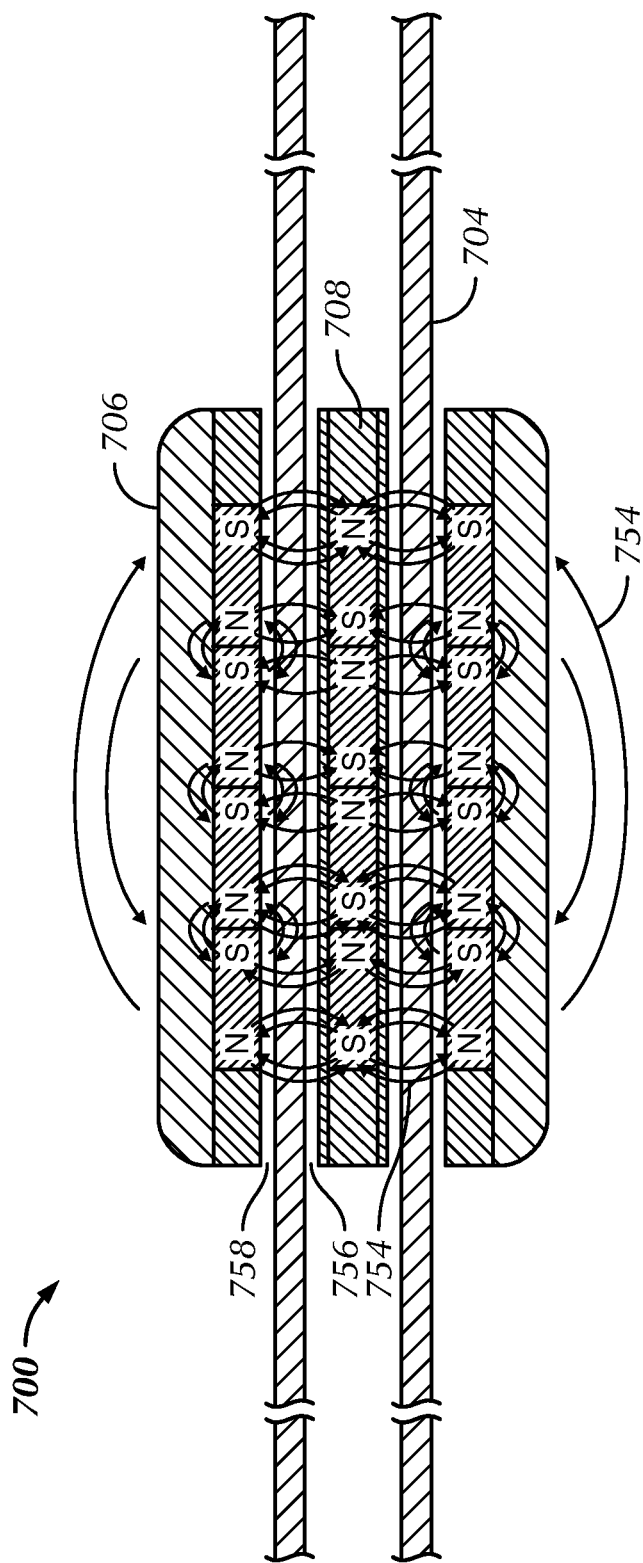
Figure 7D:
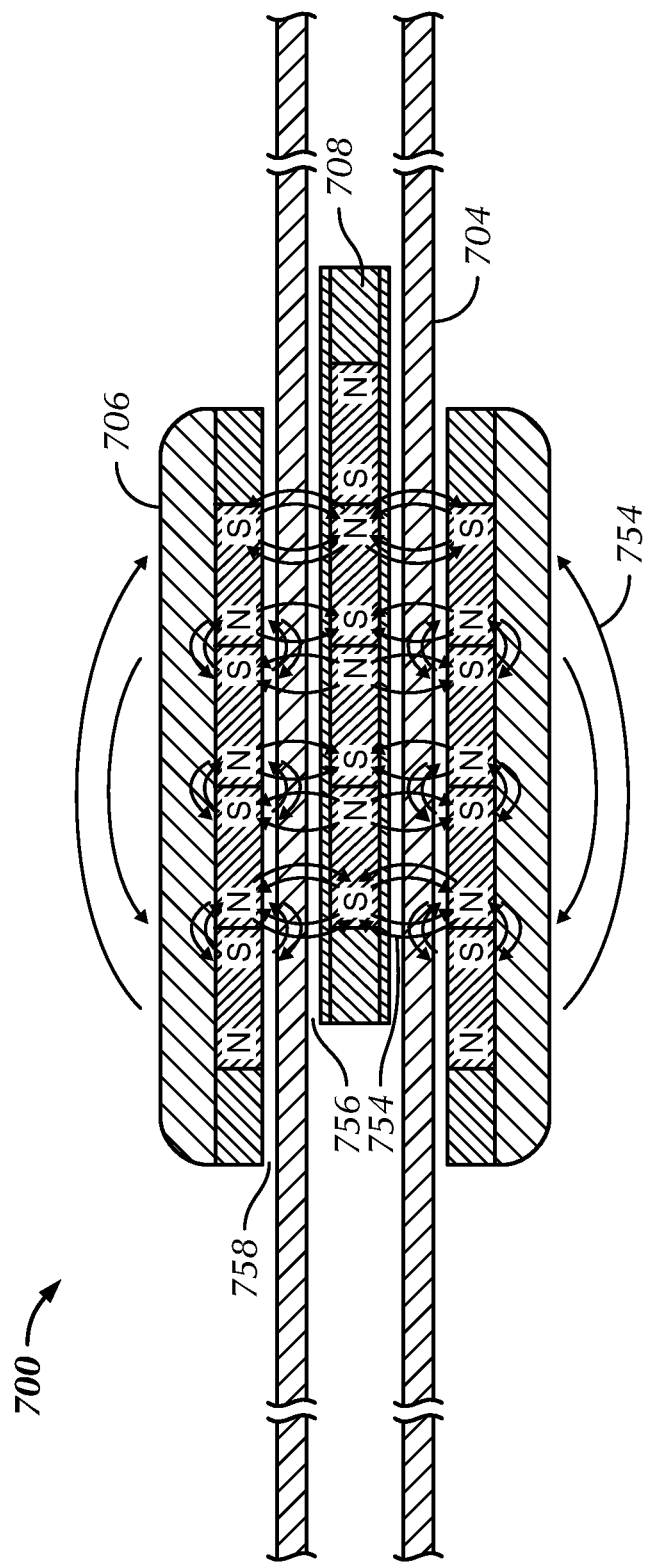

FIGS. 7A-7D illustrate, in cross-section, portions of a delivery assembly 700 and example associated magnetic fields 754. The assembly 700 can include a coaxial arrangement of an elongate tube 704, an outer magnetic member 706, and an inner magnetic member 708. The inner magnetic member 708 and the outer magnetic member 706 can start and end at about the same axial location as shown in FIGS. 7A and 7C, or the members can be slightly offset from one another as shown in FIGS. 7B and 7D. The inner magnetic member 708 can be formed with a cylindrical shape and disposed within the tube 704. An air gap 756 between the outer surface of the inner magnetic member 708 and the inner surface of the tube 704 can be as small as possible but large enough to allow the inner magnetic member 708 to move axially within the tube. The outer magnetic member 706 can be formed with a ring shape, disposed around the tube 704, and have the same or approximately the same axial length as the inner magnetic member 708. An air gap 758 between the outer magnetic member 706 and the tube 704 can be as small as possible but large enough to allow the outer magnetic member 706 to axially move along the tube 704.

Magnets of the inner magnetic member 708 and the outer magnetic member 706 can be arranged so that their opposing poles face one another. Since unlike poles attract, this arrangement makes it possible to keep adjacent magnets in close and strong contact allowing synchronous movement along the axis of the tube 704.

Magnetics of the inner magnetic member 708 and the outer magnetic member 706 can be separated by non-magnetic spacers 760, as shown in FIGS. 7A and 7B, or not separated by non-magnetic spacers 760, as shown in FIGS. 7C and 7D. Embodiments of the delivery assembly 700 that do not includes spacers 760 can have stronger coupling between the inner magnetic member 708 and the outer magnetic member 706 and can have a shorter overall length. If present, the spacers 760 can include a material that neither produces its own magnetic field nor responds to magnetic fields of other members. Example materials that can be useful for forming spacers 760 include materials used to form the elongate tube 704, such as PEBAX® block copolymer commercially available from Arkema of Colombes, France. The spacers 760 of the inner magnetic member 708 and the outer magnetic member 706 can be the same length or approximately the same length to maintain a desired alignment of poles.

The magnets of the inner magnetic member 708 and the outer magnetic member 706 can produce their own magnetic fields 754 and/or respond to nearby magnetic fields of other members. The magnetic fields 754 can be created within the inner magnetic member 708, within the outer magnetic member 706, and between the inner and outer magnetic members 706, 708. The magnetic fields 754 can be specified at any given point by a direction and a magnitude (or strength). The magnetic fields 754 can be sufficiently strong to allow the outer magnetic member 706 to guide a position of the inner magnetic member 708 through a sidewall 718 of the tube 704. Pulling back or pushing forward of the outer magnetic member 706 can cause a corresponding motion of the inner magnetic member 708. The strength of the magnetic fields 754 can depend on the number of magnets in the inner and outer magnetic members, the size of the magnets, the material composition of the magnets, the inclusion of spacers 760 and/or the proximity of the magnets. Factors to consider when designing the magnetic field 754 strength for the assembly 700 can include the thickness of the tube 704, the material used to make the tube 704, and/or the friction between the surfaces of the tube's sidewall 718 and the inner 708 or outer 706 magnetic members.

Figure 8:
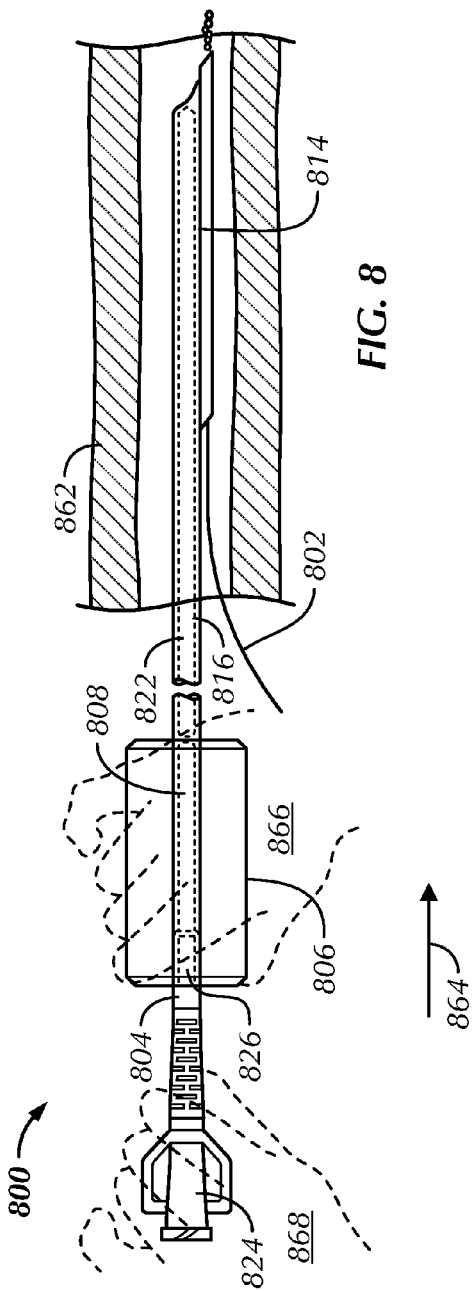
FIGS. 8-10 schematically illustrate delivery of an elongate and expandable implant into a vascular vessel using a delivery assembly and method, as constructed in accordance with at least one embodiment.
Figure 9:
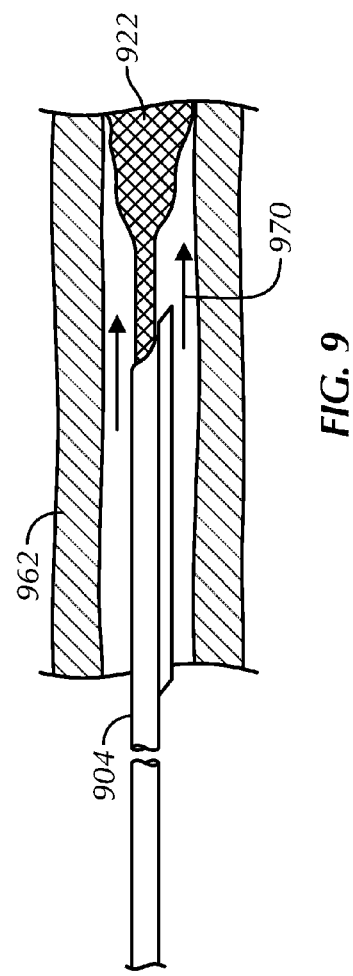
Figure 10:
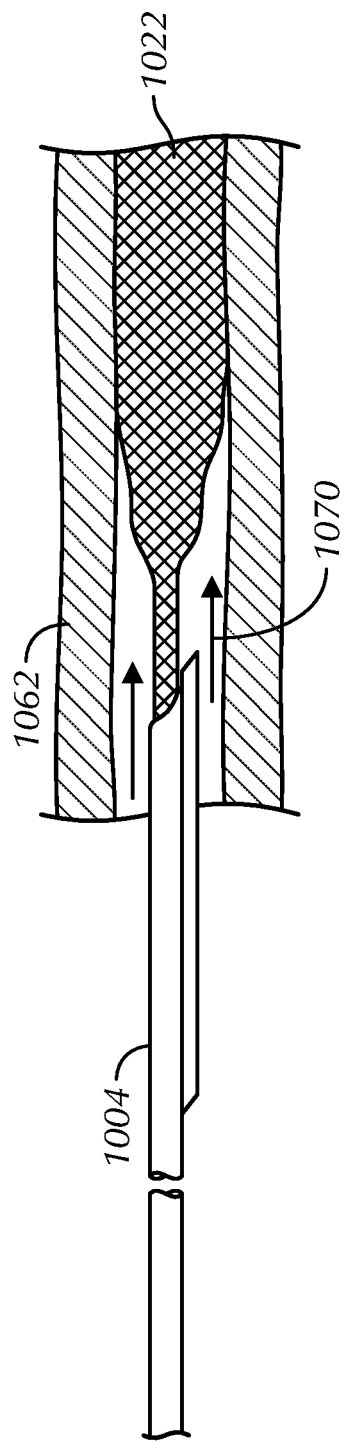

FIGS. 8-10 schematically illustrate a method for delivering an elongate or expandable implant using a present assembly.

FIG. 8 schematically illustrates an assembly 800, including an elongate tube 804, an outer magnetic member 806, an inner magnetic member 808 and an implant 822, being delivered into a vascular vessel 862 over a guidewire 802. Access to the vascular vessel 862 can be obtained by piercing an opening and inserting the guidewire 802 into the opening. The guidewire 802 can be advanced through the vascular vessel 862 to a defect site or target region. A distal end portion of the tube 804 and the implant 822 can then be inserted into the vascular vessel 862 by advancing a rapid exchange lumen 814 of the tube 804 over the guidewire 802. Through the continued application of a compressive force to the proximal end portion of the tube 804, intermediate and distal end portions of the tube 804 and the implant 822 are advanced into and through the vascular vessel 862 to the defect site or target region.

With portions of the tube 804 and implant 822 positioned within the defect site or target region, the implant 822 can be urged out the distal end of the tube 804 and into the vascular vessel 862 by the inner magnetic member 808. The inner magnetic member 808 can be driven to discharge the implant 822 from the distal end of the tube 804 by the outer magnetic member 806 and/or a compression actuator couplable to a hub 824 at the tube's proximal and portion. In the example of FIG. 8, the implant 822 can be discharged from the tube 804 and delivered to the defect site or target region by moving the outer magnetic member 806 in the distal direction 864 along the outer surface of the tube 804 with a first hand 866 and simultaneously withdrawing the tube 804 in the opposite direction with a second hand 868. The movement of the outer magnetic member 806 along the tube 804 can cause corresponding distal movement of the inner magnetic member 808 through a delivery lumen 816 due to magnetic coupling between the members. Optionally, as discussed in greater detail above, the implant 822 can be discharged from the tube 804 by applying a force to a proximal end portion 826 of the inner magnetic member 808 using a compression actuator, while maintaining a stationary position of the outer magnetic member 806.

FIGS. 9 and 10 schematically illustrate the gradual discharge of an implant 922, 1022 out the distal end portion of a tube 904, 1004 and into a vascular vessel 962, 1062 as the result of continued distal advancement of an inner magnetic member and withdrawal of the tube 904, 1004. As the implant 922, 1022 leaves the tube 904, 1004, it can expand through the absorption of bodily fluids and occlude blood flow 970, 1070 through the vascular vessel 962, 1062. After the implant 922, 1022 fully occludes the defect site or target region of interest, the tube 904, 1004 can be removed from the vascular vessel 962, 1062, and the opening can be sealed.

FIG. 11 illustrates implantation of an elongate and expandable implant 1122 located in, and occluding, a portion of a great saphenous vein 1172 of a leg 1174. In this example, the implant 1122 is placed between a point 1176 near a medial side of the leg 1174 and a point 1178 near a junction between the great saphenous vein 1172 and a femoral vein 1180. Initially disposed in a radially compressed configuration to ease insertion and even deployment, the implant 1122 can be configured to quickly expand upon discharge from of an elongate tube. The implant 1122, when wetted within the vein 1172, can expand from a first diametrical size or first cross-sectional area to a second larger diametrical size or second larger cross-sectional area. In various examples, the second larger diametrical size or second larger cross-sectional area is at least 5 times or at least 10 times the first diametrical size or first cross-sectional area.

The present inventors have found that the present assemblies and methods can advantageously be used to deliver the elongate and expandable implants disclosed in multiple commonly-owned U.S. patent applications, including Ser. No. 13/310,503, entitled "ELONGATED EXPANDABLE MEMBER FOR OCCLUDING VARICOSE VEINS" and issued as U.S. Pat. No. 8,758,427, Ser. No. 14/298,066, entitled "ELONGATED EXPANDABLE MEMBER FOR OCCLUDING VARICOSE VEINS, and Ser. No. 14/630,291, entitled "ELONGATE EXPANDABLE MEMBER FOR OCCLUDING VASCULAR VESSEL," the disclosure of each of which is hereby incorporated by reference in its entirety.

Figure 12:
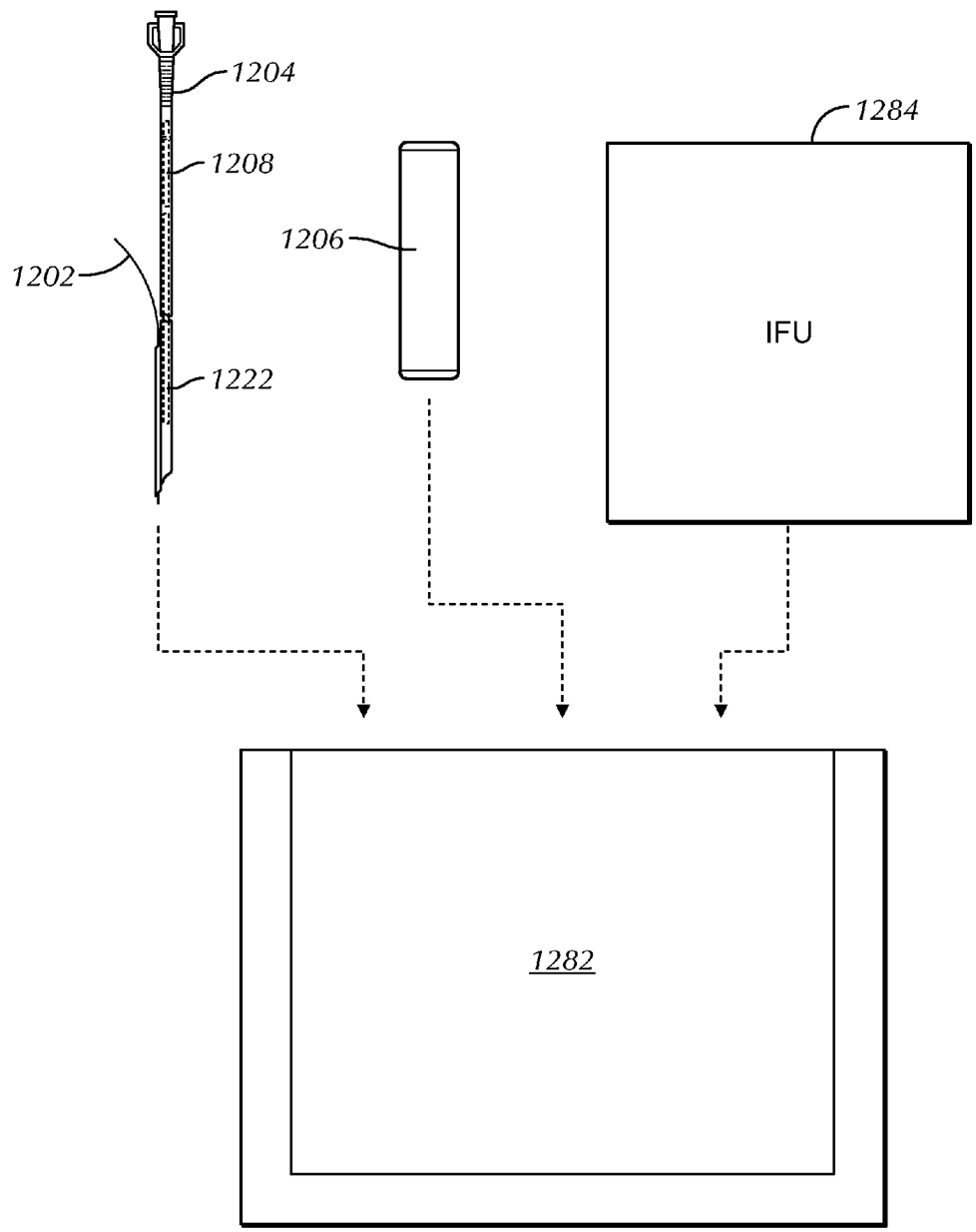
FIG. 12 schematically illustrates a delivery assembly kit, as constructed in accordance with at least one embodiment.

FIG. 12 illustrates a kit 1282 including an elongate tube 1204, an inner magnetic member 1208, an implant 1222, an outer magnetic member 1206, instructions for using the kit 1284, and, optionally, a guidewire 1202. The inner magnetic member 1208 and the implant 1222 can come preloaded in the elongate tube 1204. The outer magnetic member 1206 can be configured to be disposable or reusable.

Closing Notes:

The present inventors have discovered that delivery of elongate or expandable implants into a patient can be assisted through the use of a magnetic arrangement. This delivery assistance can be utilized by a physician during a procedure, particularly a procedure involving delivery of an elongate implant configured to expand when exposed to bodily fluids. The magnetic arrangement can include an outer magnetic member and an inner magnetic member. Each magnetic member can include a plurality of permanent magnets forming a magnetic stack. Adjacent magnets within the stacks can be arranged so that opposing poles face one another. A syringe or an inflator/deflator can be used in conjunction with the magnetic members to discharge an implant from a distal end portion of an elongate tube.

The above Detailed Description includes references to the accompanying drawings, which form a part of the Detailed Description. The Detailed Description should be read with reference to the drawings. The drawings show, by way of illustration, specific embodiments in which the present assemblies, kits and methods can be practiced. These embodiments are also referred to herein as "examples."

The above Detailed Description is intended to be illustrative and not restrictive. For example, the above-described examples (or one or more features or components thereof) can be used in combination with each other. Other embodiments can be used, such as by one of ordinary skill in the art upon reviewing the above Detailed Description. Also, various features or components have been or can be grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, a delivery assembly can comprise an elongate tube, an outer magnetic member, and an inner magnetic member. The elongate tube can extend from a proximal end portion to a distal end portion and defines a delivery lumen. The outer magnetic member can be movable along an outer surface of the tube, and the inner magnetic member is positioned within the delivery lumen and is magnetically coupled to the outer magnetic member through a sidewall of the tube. The inner magnetic member can be movable through the delivery lumen when actuated by relative movement between the outer magnetic member and the tube.

In Example 2, the delivery assembly of Example optionally further comprises a syringe or an inflator/deflator couplable to a hub at the proximal end portion of the tube.

In Example 3, the delivery assembly of any one or any combination of Examples 1 and 2 optionally further comprises an implant positioned within the delivery lumen of the tube, distal to the inner magnetic member.

In Example 4, the delivery assembly of Example 3 can optionally be configured such that the implant is an elongate expandable member for occluding a vascular vessel.

In Example 5, the delivery assembly of any one or any combination of Examples 1-4 can optionally be configured such that the outer magnetic member is sized and shaped to surround a portion of the tube.

In Example 6, the delivery assembly of any one or any combination of Examples 1-5 can optionally be configured such that the tube, the inner magnetic member, and the outer magnetic member are coaxial.

In Example 7, the delivery assembly of any one or any combination of Examples 1-6 can optionally be configured such that the outer magnetic member includes a plurality of permanent magnets forming a magnetic stack. Adjacent permanent magnets of the magnetic stack can be arranged so that opposing poles face one another.

In Example 8, the delivery assembly of Example 7 can optionally be configured such that the outer magnetic member includes a tube surrounding an outer surface of the magnetic stack.

In Example 9, the delivery assembly of any one or any combination of Examples 7 and 8 can optionally be configured such that the magnetic stack is bounded on its ends by a non-magnetic member.

In Example 10, the delivery assembly of any one or any combination of Examples 7-9 can optionally be configured such that one or more permanent magnets of the magnetic stack are separated by one or more non-magnetic spacer members.

In Example 11, the delivery assembly of Example 10 can optionally be configured such that adjacent permanent magnets of the magnetic stack are separated by a non-magnetic spacer member.

In Example 12, the delivery assembly of any one or any combination of Examples 7-11 is optionally configured such that the plurality of permanent magnets of the magnetic stack includes one or more of neodymium, samarium cobalt, ceramic, or alnico.

In Example 13, the delivery assembly of any one or any combination of Examples 1-12 can optionally be configured such that the inner magnetic member includes a plurality of permanent magnets forming a magnetic stack. Adjacent permanent magnets of the magnetic stack can be arranged so that opposing poles face one another.

In Example 14, the delivery assembly of Example 13 can optionally be configured such that the inner magnetic member includes a hypotube surrounding an outer surface of the magnetic stack.

In Example 15, the delivery assembly of any one or any combination of Examples 13 and 14 can optionally be configured such that the magnetic stack is bounded on its ends by a non-magnetic member.

In Example 16, the delivery assembly of any one or any combination of Examples 13-15 can optionally be configured such that one or more permanent magnets of the magnetic stack are separated by one or more non-magnetic spacer members.

In Example 17, the delivery assembly of Example 16 can optionally be configured such that adjacent permanent magnets of the magnetic stack are separated by a non-magnetic spacer member.

In Example 18, the delivery assembly of Example 17 can optionally be configured such that the non-magnetic spacer member of the inner magnetic member includes a length about equal to a length of a non-magnetic spacer of the outer magnetic member.

In Example 19, the delivery assembly of any one or any combination of Examples 13-18 can optionally be configured such that the plurality of permanent magnets of the magnetic stack includes one or more of neodymium, samarium cobalt, ceramic, or alnico.

In Example 20, the delivery assembly of any one or any combination of Examples 1-19 can optionally further comprise an elastomeric member surrounding a portion of the inner magnetic member. The elastomeric member can provide a seal between an outer surface of the inner magnetic member and an inner surface of the tube.

In Example 21, the delivery assembly of any one or any combination of Examples 1-20 can optionally be configured such that the sidewall of the tube at its distal end portion includes one or more pressure dissipation holes.

In Example 22, the delivery assembly of any one or any combination of Examples 1-21 can optionally be configured such that the distal end portion of the tube includes a rapid exchange lumen extending generally parallel with the delivery lumen. The rapid exchange lumen can be sized and shaped to receive a guidewire.

In Example 23, the delivery assembly of any one or any combination of Examples 1-22 can optionally be configured such that the distal end portion of the tube is skived.

In Example 24, a method can comprise delivering an implant into a vascular vessel. The vascular vessel can be accessed by piercing an opening and inserting a guidewire into the opening. The guidewire can be advanced through a portion of the vascular vessel to a defect site or target region. A distal end portion of an elongate tube and an implant, which is positioned within a delivery lumen of the tube, can be inserted into the vascular vessel and advanced to the defect site or target region. Once at the defect site or target region, relative movement between the inner magnetic member, which is positioned within the delivery lumen and proximal to the implant, and the tube can be generated to urge portions of the implant out the distal end portion of the tube and into the vascular vessel.

In Example 25, the method of Example 24 can optionally be configured such that inserting the distal end portion of the tube and the implant into the vascular vessel includes advancing a rapid exchange lumen, located at the distal end portion of the tube, over the guidewire.

In Example 26, the method of any one or any combination of Examples 24 and 25 can optionally be configured such that generating relative movement between the inner magnetic member and the tube includes moving an outer magnetic member, which is positioned at least partially around the tube, relative to the tube and creating a movable magnetic field through a sidewall of the tube.

In Example 27, the method of Example 26 can optionally be configured such that moving the outer magnetic member relative to the tube includes causing the relative movement between the inner magnetic member and the tube.

In Example 28, the method of any one or any combination of Examples 24-27 can optionally be configured such that generating relative movement between the inner magnetic member and the tube includes urging fluid against a proximal end portion of the inner magnetic member using a syringe or an inflator/deflator, which is coupled to a proximal end portion of the tube, while maintaining a magnetic coupling between a static outer magnetic member, which is positioned at least partially around the tube, and the inner magnetic member.

In Example 29, the method of Example 28 can optionally be configured such that urging fluid against the proximal end portion of the inner magnetic member while maintaining the magnetic coupling between the static outer magnetic member and the inner magnetic member causes the intermediate and distal end portions of the tube to move proximally.

In Example 30, the method of any one or any combination of Examples 24-29 can optionally be configured such that urging portions of the implant out the distal end portion of the tube and into the vascular vessel includes inserting an elongate and expandable member in the vascular vessel to occlude blood flow through the vascular vessel.

In Example 31, the method of any one or any combination of Examples 24-30 optionally further comprises removing the tube from the vascular vessel and sealing the opening after portions of the implant are urged out the distal end portion of the tube a desired amount.

In Example 32, the assembly or method of any one or any combination of Examples 1-31 can optionally be configured such that all elements or options recited are available to use or select from.

Certain terms are used throughout this patent document to refer to particular features or components. As one skilled in the art appreciates, different people may refer to the same feature or component by different names. This patent document does not intend to distinguish between components or features that differ in name but not in function.

For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" refers to a range of numbers that one of skill in the art would consider equivalent to the recited value (e.g., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to a physician. "Distal" and "distally" refer to a position that is distant from, or in a direction away from, the physician. "Proximal" and "proximally" refer to a position that is near, or in a direction toward, the treating physician. And finally, the phrase "magnetic member," as used in "inner magnetic member" and "outer magnetic member" refers to a member including a material that produces its own magnetic field, responds to a magnetic field of another member, or both produces its own magnetic field and responds to a magnetic field of another member.

The scope of the present assemblies, kits and methods should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, an assembly, kit or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A delivery assembly, comprising:
    an elongate tube extending from a proximal end portion to a distal end portion and defining a delivery lumen;
    an outer magnetic member movable along an outer surface of the tube;
    an inner magnetic member positioned within the delivery lumen and magnetically coupled to the outer magnetic member through a sidewall of the tube; and
    an implant positioned within the delivery lumen and distal to the inner magnetic member,
    the inner magnetic member movable through the delivery lumen when actuated by relative movement between the outer magnetic member and the tube.

2. The delivery assembly of claim 1, further comprising a syringe or an inflator/deflator couplable to a hub at the proximal end portion of the tube.

3. The delivery assembly of claim 1, wherein the implant is an elongate and expandable member for occluding a vascular vessel.

4. The delivery assembly of claim 1, wherein the outer magnetic member is sized and shaped to surround a portion of the tube.

5. The delivery assembly of claim 1, wherein the tube, the inner magnetic member, and the outer magnetic member are coaxial.

6. The delivery assembly of claim 1, wherein the sidewall of the tube at its distal end portion includes one or more pressure dissipation holes.

7. The delivery assembly of claim 1, wherein the distal end portion of the tube includes a rapid exchange lumen extending generally parallel with the delivery lumen; and wherein the rapid exchange lumen is sized and shaped to receive a guidewire.

8. The delivery assembly of claim 1, wherein the distal end portion of the tube is skived.

9. A delivery assembly, comprising:
    an elongate tube extending from a proximal end portion to a distal end portion and defining a delivery lumen;
    an outer magnetic member movable along an outer surface of the tube; and
    an inner magnetic member positioned within the delivery lumen and magnetically coupled to the outer magnetic member through a sidewall of the tube,
    the inner magnetic member movable through the delivery lumen when actuated by relative movement between the outer magnetic member and the tube, and
    one or both of the outer magnetic member or the inner magnetic member including a plurality of permanent magnets forming a magnetic stack, adjacent permanent magnets of the magnetic stack being arranged so that opposing poles face one another.

10. The delivery assembly of claim 9, further comprising a syringe or an inflator/deflator couplable to a hub at the proximal end portion of the tube.

11. The delivery assembly of claim 9, further comprising an implant positioned within the delivery lumen and distal to the inner magnetic member.

12. The delivery assembly of claim 9, wherein the outer magnetic member is sized and shaped to surround a portion of the tube.

13. The delivery assembly of claim 9, wherein the plurality of permanent magnets of the magnetic stack is separated by one or more non-magnetic spacer members.

14. The delivery assembly of claim 9, further comprising an elastomeric member surrounding a portion of the inner magnetic member, the elastomeric member providing a seal between an outer surface of the inner magnetic member and an inner surface of the tube.

15. The delivery assembly of claim 9, wherein the distal end portion of the tube includes a rapid exchange lumen extending generally parallel with the delivery lumen; and wherein the rapid exchange lumen is sized and shaped to receive a guidewire.

16. A delivery assembly, comprising:
an elongate tube extending from a proximal end portion to a distal end portion and defining a delivery lumen;
an outer magnetic member movable along an outer surface of the tube; and
an inner magnetic member positioned within the delivery lumen and magnetically coupled to the outer magnetic member through a sidewall of the tube,
the inner magnetic member movable through the delivery lumen when actuated by relative movement between the outer magnetic member and the tube, and
the sidewall of the tube includes one or more pressure dissipation holes at its distal end portion.

17. The delivery assembly of claim 16, further comprising a syringe or an inflator/deflator couplable to a hub at the proximal end portion of the tube.

18. The delivery assembly of claim 16, further comprising an implant positioned within the delivery lumen and distal to the inner magnetic member.

19. The delivery assembly of claim 18, wherein the implant is an elongate and expandable member for occluding a vascular vessel.

20. The delivery assembly of claim 16, wherein the outer magnetic member is sized and shaped to surround a portion of the tube.

21. The delivery assembly of claim 16, wherein the distal end portion of the tube includes a rapid exchange lumen extending generally parallel with the delivery lumen; and wherein the rapid exchange lumen is sized and shaped to receive a guidewire.

22. The delivery assembly of claim 16, wherein the distal end portion of the tube is skived.

* * * * *